United States Patent [19]

Tanaka

[11] Patent Number: 5,540,921
[45] Date of Patent: Jul. 30, 1996

[54] SOLID O/W-TYPE COSMETIC COMPOSITION

[75] Inventor: Yoichiro Tanaka, Tokyo, Japan

[73] Assignee: KOSÉ Corporation, Tokyo, Japan

[21] Appl. No.: 171,615

[22] Filed: Dec. 22, 1993

[30] Foreign Application Priority Data

Mar. 10, 1993 [JP] Japan ................. 5-016236 U
Jun. 29, 1993 [JP] Japan ................... 5-182237

[51] Int. Cl.⁶ .................. A61K 7/00; A61K 9/00
[52] U.S. Cl. .................. 424/401; 424/488; 514/777
[58] Field of Search ................... 424/401, 484, 424/485, 488, 78.02, 78.08, 78.03, 500, 499; 514/777

[56] References Cited

U.S. PATENT DOCUMENTS

| | | | |
|---|---|---|---|
| 3,903,345 | 9/1975 | Baker et al. | |
| 4,367,609 | 1/1983 | Lloyd | 47/57.6 |
| 4,459,285 | 7/1984 | Grollier et al. | 424/74 |
| 4,703,041 | 10/1987 | Weber et al. | 514/23 |
| 4,728,210 | 3/1988 | Barish et al. | |
| 4,985,250 | 1/1991 | Bee et al. | 424/401 |
| 5,098,891 | 3/1992 | Hammarström et al. | 514/21 |
| 5,171,815 | 12/1992 | Magill et al. | 526/348.1 |
| 5,219,560 | 6/1993 | Suzuki et al. | 424/63 |

FOREIGN PATENT DOCUMENTS

| | | |
|---|---|---|
| 0317899 | 5/1989 | European Pat. Off. . |
| 0522624 | 1/1993 | European Pat. Off. . |
| 2573290 | 5/1986 | France . |
| 3-141211 | 6/1991 | Japan . |
| 4-305513 | 10/1992 | Japan . |
| 5-32521 | 2/1993 | Japan . |
| 5-178723 | 7/1993 | Japan . |

OTHER PUBLICATIONS

Database WPI, Derwent Publications, AN-79-900088, JP-54-095668, Jul. 28, 1979.
Database WPAT, AN-88-052550/08, JP-63-007757, Jan. 13, 1988.

*Primary Examiner*—Jeffrey Mullis
*Attorney, Agent, or Firm*—Oblon, Spivak, McClelland, Maier & Neustadt, P.C.

[57] ABSTRACT

A solid o/w-type cosmetic composition, a process for molding it, and a container used for aqueous-type solid cosmetics are disclosed. The cosmetic composition comprises (a) a water-soluble solidifying agent selected from agar and gelatin, (b) an oil component and (c) water, and optionally, (d) a powder or (e) a water-soluble adhesive. The composition has superior characteristics inherent in an o/w-type cosmetic, while providing excellent usability and portability. The molding process comprises applying a water-carrying sheet material to the surface of the composition before solidification and releasing it after solidification. The container for an aqueous-type solid cosmetic composition is characterized by having a water-absorbing material secured to a receptacle of the container.

4 Claims, 3 Drawing Sheets

SOLID O/W-TYPE COSMETIC COMPOSITION

BACKGROUND OF THE INVENTION

1. Field of the Invention

The present invention relates to a solid oil-in-water type (o/w-type) cosmetic composition, and, more particularly, to a solid o/w-type cosmetic composition which imparts a fresh feel on use, exhibits good affinity to the skin, gives a natural make-up finish, possesses superior moisturizing properties, provides excellent ease of application, and is convenient to carry. Further, the present invention relates to a process for molding this o/w-type solid cosmetic composition and to a container useful for aqueous-type solid cosmetic compositions such as the cosmetic composition of the present invention.

2. Description of the Background Art

Water-in-oil type (w/o-type) cosmetic compositions are conventionally known as a solid cosmetic composition containing water. Although these solid w/o-type cosmetic compositions are excellent in treatment characteristics such as skin protection capability and softness, they lack in freshness. They are sticky and oily, and do not impart a satisfactory intimate feel to the skin.

On the other hand, o/w-type cosmetic compositions are highly evaluated due to the fresh feel on use, intimate feel to the skin, and natural make-up finish. However, because o/w-type cosmetic compositions are normally liquid or creamy, they must be stored in containers such as bottles or tubes, for which the openings must be tightly sealed with a cap or the like. Thus, they are inconvenient to use and to carry around.

Development of a solid o/w-type cosmetic composition having excellent cosmetic characteristics inherent in the o/w-type and adaptable to filling into a container which is handy, portable and convenient to use has been therefore desired.

In view of this situation, the present inventors have undertaken extensive studies and found that a cosmetic composition obtained by solidifying a composition comprising a specific water-soluble solidifying agent, an oil component and water, and, optionally, a powder and a water-soluble adhesive, possesses both the excellent cosmetic characteristics inherent in o/w-type cosmetics and superior usability and portability.

The present inventors have further found that the usability can be improved if the cosmetic composition is molded so as to have a noncontinuous surface after solidification.

Furthermore, the present inventors have found that this usability can be improved even more if the cosmetic composition is filled in a container which can absorb water oozing therefrom.

SUMMARY OF THE INVENTION

Accordingly, an object of the present invention is to provide a solid o/w-type cosmetic composition comprising (a) a water-soluble solidifying agent selected from the group consisting of agar and gelatin, (b) an oil component and (c) water.

Another object of the present invention is to provide a solid o/w-type cosmetic composition comprising, in addition to the above components (a), (b) and (c), (d) a powder or (e) a water-soluble adhesive, or both.

Still another object of the present invention is to provide a process for molding a solid o/w-type cosmetic composition which comprises, applying a water-carrying sheet material to the surface of an o/w-type cosmetic composition before solidification, solidifying the o/w-type cosmetic composition by cooling, and releasing said water-carrying sheet material.

A further object of the present invention is to provide a container for an aqueous-type solid cosmetic composition characterized by having a water-absorbing material secured to a receptacle thereof in which the aqueous-type solid cosmetic composition is contained.

Other and further objects, features and advantages of the present invention will be more fully evident from the following description.

DETAILED DESCRIPTION OF THE INVENTION AND PREFERRED EMBODIMENTS

Figure 1:
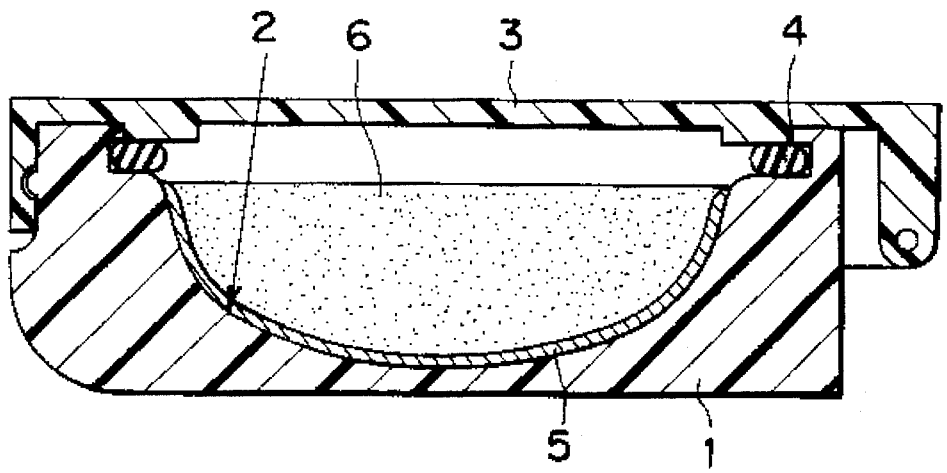
FIG. 1 is a cross-sectional view of the container of the present invention.

The water-soluble solidifying agent which is component (a) used in preparing the solid o/w-type cosmetic composition of the present invention functions so as to solidify the cosmetic composition and to provide hardness required for it to be convenient to use and to be portable.

This water-soluble solidifying agent is selected from agar and gelatin, with no restrictions as to their origin or the areas where they have been produced. Agar is preferred in view of a better sensation to the touch upon use.

The amount of component (a) in the composition is normally about 0.1 to 10% by weight ("% by weight" is hereinafter referred to simply as "%"), and preferably 0.3 to 7%. If the amount of component (a) is less than 0.1%, sufficient hardness of the solidified cosmetic composition cannot be obtained; if it is greater than 10%, the composition is too hard, does not impart the intended watery, fresh sensation, and does not extend well, resulting in an incomplete, non-uniform make-up finish.

There are no limitations to the oil component which is used as component (b) of the present invention. Any oils which are commonly used in cosmetics including solid, semi-solid or liquid oils, such as various vegetable oils, animal oils, mineral oils and synthetic oils, can be used.

Specific examples of the oil components include oils and fats such as olive oil, jojoba oil and mink oil; waxes such as beeswax and candellila wax; hydrocarbons such as liquid paraffin, microcrystalline wax and petrolatum; fatty acids such as stearic acid and oleic acid; higher alcohols such as cetanol; esters such as isopropyl myristate; lanolin derivatives such as isopropyl lanolin fatty acid and lanolin alcohol; esters of starch fatty acid; silicone compounds such as methylpolysiloxane, methylphenylpolysiloxane, and dimethylpolysiloxane polymers having a three dimensional cross-linked structure; and the like.

These oil components may be used either singly or in combination of two or more. It is desirable that they be incorporated in an amount of about 0.5 to 30%, particularly 1 to 20%, in the composition of the present invention.

If this amount is smaller than 0.5%, close fitness to the skin and water resistance of the make-up films are insufficient; if greater than 30%, the composition does not impart the intended watery, fresh sensation, but gives an oily and sticky feel.

Water, which is component (c) of the present invention, is used preferably in an amount of about 40 to 95%, and particularly preferably about 50 to 80%.

In the case where the o/w-type cosmetic composition of the present invention is used as foundation or eyeshadow and the like, it is necessary that a powder, as component (d), be incorporated in addition to said essential components.

There are no specific limitations as to the kind of powder used in the present invention, so long as the same is a commonly used cosmetic powder. Given as examples of such cosmetic powders are titanium dioxide, talc, mica, kaolin, magnesium carbonate, calcium carbonate, aluminum silicate, magnesium silicate, calcium silicate, zinc oxide, red iron oxide, yellow iron oxide, black iron oxide, ultramarine blue, prussian blue, tar pigment, natural pigments, titanated mica, iron oxide titanated mica, bismuth oxychloride, nylon powder, silk powder and the like.

Powders provided with water repellency by a hydrophobic treatment can be used also as component (d). Fluorine compounds, silicone oils, metallic soaps, waxes, oils and fats, hydrocarbons and the like can be given as materials for the hydrophobic treatment.

These cosmetic powders may be used in an amount of 1 to 40%, and preferably 3 to 30%.

Furthermore, a water-soluble adhesive may be added as component (e), as required.

The water-soluble adhesive is a water-soluble polymer compound which does not solidify by itself, but exhibits actions to supplement the strength of the gel formed by a water-soluble solidifying agent which is component (a).

Given as examples of such water-soluble adhesives are cellulose derivatives such as methylcellulose, hydroxymethylcellulose, hydroxyethylcellulose, hydroxypropylcellulose and carboxymethylcellulose; naturally occurring polymers such as sodium arginate, carrageenan, quince seed gum, xanthane gum and pectin; synthetic polymer compounds such as polyvinyl alcohol, carboxyvinyl polymer, sodium polyacrylate, sodium polymethacrylate, polyacrylic acid glycerine ester and polyvinyl pyrrolidone; and the like. These water-soluble adhesives may be added in an amount of 0.05 to 2.0%, and preferably 0.1 to 1.0%.

Other components which are commonly used in cosmetics, such as moisturizers, preservatives, antioxidants, UV absorbers, skin-improvers, perfumes, surfactants, lower primary alcohols, lower polyhydric alcohols and clay minerals, can be added to the o/w-type cosmetic composition to the extent that the effects of the present invention are not adversely affected.

The solid o/w-type cosmetic composition can be prepared by emulsifying components (b) and (c) into an o/w-type emulsion by a conventional method, adding component (d) or other optional components as needed, and solidifying the mixture with the addition of component (a) and, if necessary, component (e).

In one embodiment of the preparation of the cosmetic composition of the present invention, component (a) (and component (e)) are dissolved in component (c) with heating, this solution is mixed with component (b) and, optionally component (d), while stirring, and any desired optional components are further added to the mixture. Following this, the mixture is filled into a container and cooled to solidify.

Because of the inherent nature of the water-soluble solidifying agent which is incorporated in the o/w-type cosmetic composition as an essential component, the composition of the present invention as solidified presents a smooth continuous surface for which the structure is different from that inside the composition. When the composition is filled into a container and prepared into a product of the type, for example, such as a foundation, of which a small portion is taken by an applicator such as a sponge, this smooth continuous surface causes the applicator to slip over it and prevents the cosmetic from being used.

In such an instance, exposing the inside texture of the cosmetic as the surface, for example, by mechanically cutting out the molded surface, may achieve the objective. However, this objective can be achieved more advantageously by the application of the molding method which has been developed by the present inventor.

Specifically, it is possible to have the inside texture exposed as the surface of the cosmetic composition and to produce a minute irregular non-continuous layer on the surface by applying a water-carrying sheet material to the surface of the o/w-type cosmetic composition after it has been filled into a container, such as a metal dish, and before it is solidified, then solidifying this cosmetic composition by cooling, and releasing said water-carrying sheet material. The surface of the cosmetic composition thus produced greatly promotes ease of application of the cosmetic composition.

Any materials which can contain a certain amount of water, such as meshes, non-woven textiles, textiles and papers, can be used as the water-carrying sheet material for the molding process of the present invention. Because the affinity of the cosmetic composition to the sheet material is affected by the amount of water contained in the latter, the water-carrying ability of the sheet materials should be taken into account in selecting types of this material used.

If the water-carrying ability of the sheet material is poor and the amount of water contained therein is too small, it is impossible to expose the inside texture of the cosmetic composition. Even if irregularities are externally seen to have been produced on the surface, the surface actually is found to remain smooth when observed minutely. The cosmetic composition with such a surface is difficult to attach to an applicator such as sponge. Too great water-carrying ability, on the other hand, causes too much water to be transferred from the cosmetic composition to the sheet material. This causes the cosmetic composition to dry up and to adhere to the sheet material, and eventually makes it difficult to smoothly release the sheet material after solidification of the cosmetic composition by cooling. In this case, the surface of the cosmetic after release of the sheet material may be unduly rough and uneven so that its commercial value may be lost.

As a result of tests on various textile materials in order to investigate a suitable material for use in the molding process of the present invention, those having a water-carrying rate of about 10 to 250%, preferably about 30 to 200%, as calculated by the following equation, were found to be usable as the water-carrying sheet material in the present invention irrespective of the type of material.

Water-carrying rate $(\%)=[(W_2-W_1)/W_1]\times 100$ wherein $W_1$ is the dry weight of the material and $W_2$ is the weight when water is contained.

Any materials irrespective of the type of the material, including textiles made of fibers such as acetate, nylon, polyester, acryl, polypropylene or mixtures of these fibers, can be suitably used as the water-carrying sheet material in the present invention, so long as they satisfy the water-carrying rate of the above range.

The solid o/w-type cosmetic composition obtained by the method mentioned above is made up of a texture in which oil components are dispersed in an aqueous phase. Because it is solid with no fluidity in the temperature range (0° to 50° C.) at which it is normally stored or used, the product is handy and readily portable, while preserving the excellent cosmetic characteristics inherent in an o/w-type cosmetic composition.

The o/w-type cosmetic composition of the present invention therefore can be used with special advantage as solid cosmetic products such as base creams, sun screening creams, foundations, eyeshadows, and rouge.

A container which can be used with advantage for aqueous-type solid cosmetic compositions, including the solid o/w-type cosmetic composition of the present invention, will now be illustrated.

Conventionally, most solid cosmetics such as foundations have been of the non-aqueous type, such as a powder type and an oil type. If an aqueous-type solid cosmetic composition, such as the solid o/w-type cosmetic composition of the present invention, from which water may ooze, is filled into a container used for conventional non-aqueous type cosmetics, the oozing water cannot be absorbed by the container and may weaken the adhesion strength between the cosmetic composition and the container. The cosmetic composition may rotate in the container or be released from the container, preventing the cosmetics from being entirely used up. The oozing water may not only spoil the inside of the container, but blemish the outside of the container.

In the container for aqueous-type solid cosmetic compositions of the present invention, a water absorbing material is secured to a part or whole of the container into which the aqueous-type solid cosmetic composition is filled. This water absorbing material can solve the above-mentioned problem by absorbing water oozing out from the aqueous-type solid cosmetic composition and by increasing the adhesion strength between the cosmetic composition and the container.

Any water absorbing materials which have affinity to aqueous-type solid cosmetic compositions and can absorb excess water which oozes out from the cosmetic composition can be used as the water absorbing materials in the present invention. Examples of preferable materials include textiles made of fibers such as rayon, cotton or linen; non-woven textiles made of rayon or cotton; papers such as filter paper and Japanese paper; powders such as kaolin, calcium carbonate, gypsum or alumina; water-absorbing polymers; and composite materials prepared by the combination of these materials. Layered materials prepared by laminating these water-absorbing materials also may be used. The water-absorbing materials can be secured to the container using an adhesive or by the inmold method when the container is molded.

The container for aqueous-type solid cosmetic compositions of the present invention will now be illustrated with reference to the drawings.

FIG. 1 is a cross-sectional view of a container for aqueous-type solid cosmetic compositions of the present invention, showing container body 1 which forms a receptacle 2 into which the contents are filled. A cover 3 is attached to the container body 1 so as to open or close the container. The container body 1 is further provided with a packing member 4 so as to tightly seal the container when the cover 3 is in the closed position. Various known methods can be applicable as a means for tightly sealing the contents. Of course, it is possible to fill in a compact. The receptacle 2 has secured thereto a water-absorbing material 5, upon which the aqueous-type solid cosmetic composition 6 is held.

FIGS. 2 to 5 are drawings schematically illustrating a method of securing the water-absorbing material 5 to the receptacle 2 of the container body 1.

Figure 2:
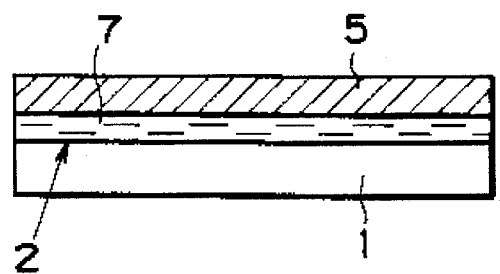
FIGS. 2 to 5 are drawings schematically illustrating a method of securing a water-absorbing material to a receptacle in which the aqueous-type solid cosmetic composition is contained.
Figure 3:
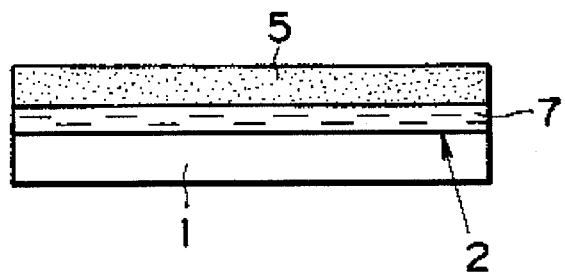
Figure 4:
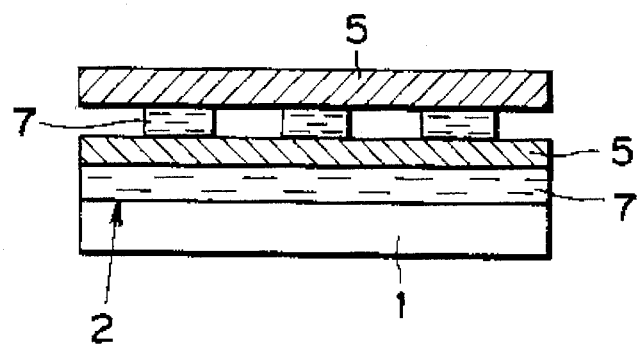
Figure 5:
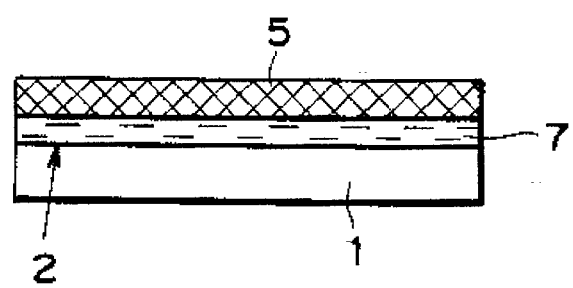

FIG. 2 shows a water-absorbing material 5, such as non-woven textile or paper, affixed via an adhesive layer 7. FIG. 3 shows a water-absorbing material 5, which is a water-absorbing powder, affixed via an adhesive layer 7. FIG. 4 shows a multi-layered water-absorbing material, in which a water absorbing polymer 5 is first affixed via an adhesive layer 7, and then over this polymer 5 is partly provided another adhesive layer 7, to which another water-absorbing material 5, such as a non-woven textile or paper, is secured. FIG. 5 shows a composite water-absorbing material 5, which consists of a non-woven textile or paper impregnated with a water absorbing polymer, affixed to the receptacle 2 via an adhesive layer 7. The surface obtained after affixing the water-absorbing material is preferably irregular rather than flat and smooth.

Figure 6:
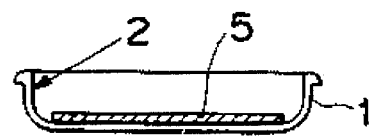
FIGS. 6 to 8 are drawings showing in cross-section locations in the container where the water-absorbing material is secured.
Figure 7:
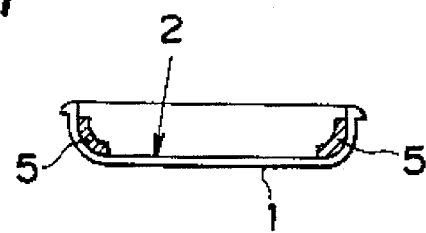
Figure 8:
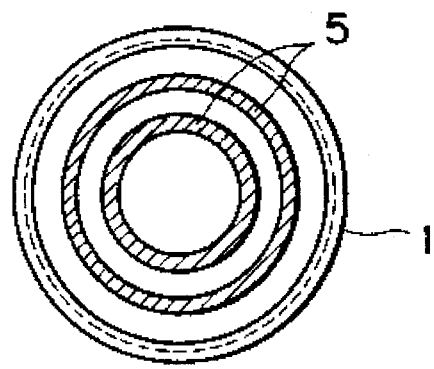

There are no specific restrictions as to the locations where water-absorbing material 5 is affixed to the receptacle 2. It can be secured so as to entirely cover the internal surface of container body 1; to cover the entire bottom surface as shown in FIG. 6; or to cover only the side wall as shown in FIG. 7. Alternatively, it is possible to form concentric circles of the water-absorbing material 5 secured to the inside of receptacle 2 of the container body 1 as shown in FIG. 8. Thus, the water-absorbing material 5 need not cover entire internal surface of the container body; it is possible to provide any desired pattern of the water-absorbing material in addition to those shown in FIGS. 6 to 8.

Polyethylene terephthalate (PET), aluminum, polypropylene (PP), AS resin, ABS resin and the like can be used as a material for the receptacle 2 where aqueous-type solid cosmetic compositions are filled into the container 1. Other materials and any combinations of these materials can also be used.

Figure 9:
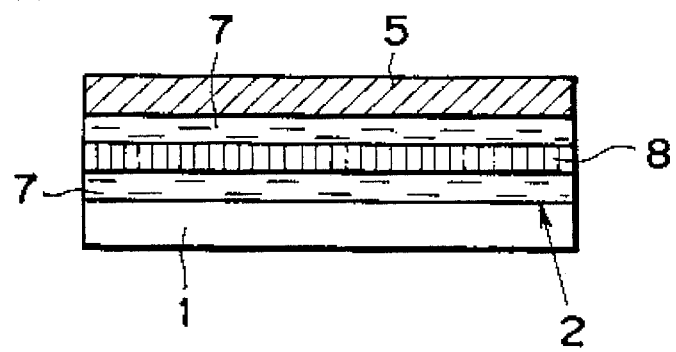
FIG. 9 shows a cross-section of part of the container, wherein an aluminum foil is provided underneath the water-absorbing material.

FIG. 9 shows an embodiment in which PET is used for the receptacle 2, over which an aluminum foil 8 is attached for water-proofing, and over this aluminum foil 8 is affixed the water-absorbing material 5, such as a non-woven textile or paper, via an adhesive layer 7.

Figure 10:
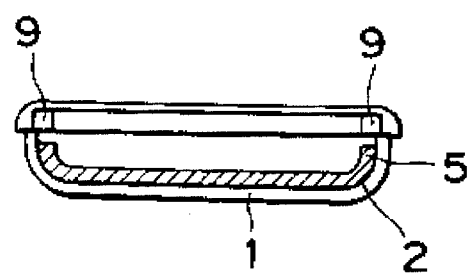
FIG. 10 shows a cross-section of a dish-like container of the present invention, which is provided with a brim around the periphery thereof.

There are no specific limitations as to the shape of the receptacle 2 inasmuch as aqueous-type solid cosmetic compositions can be filled and stored therein. It is possible to provide a projecting brim 9 around the inside periphery thereof as shown in FIG. 10 so as to prevent the content from dropping out. A rib also can be provided for drop-proofing.

Other features of the invention will become apparent in the following description of the exemplary embodiment which is given for illustration of the invention and is not intended to be limiting thereof.

EXAMPLE

Examples 1–3, Comparative Examples 1–4

<Foundations>

O/w-type foundations were prepared from components listed in Table 1 according to the method described below.

(Method of preparation)

A. Components (11) to (19) were heated and dissolved.
B. Components (1) to (9) were added to the solution A and blended to disperse.
C. After the addition of component (10), the dispersion B was filled in a container and cooled. In filling the o/w-type cosmetic compositions, a sheet of a water-carrying material was applied over the surface of the composition filled in a container and this sheet was peeled off after the composition has been solidified.

TABLE 1

| | (Formulation) % by weight | | | | | | |
|---|---|---|---|---|---|---|---|
| | Example | | | Comparative Example | | | |
| Component | 1 | 2 | 3 | 1 | 2 | 3 | 4 |
| (1) Titanium dioxide | 7.0 | — | — | 7.0 | — | — | — |
| (2) Talc | 5.0 | — | — | 5.0 | — | — | — |
| (3) Titanium dioxide treated with a fluorine compound* | — | 7.0 | 7.0 | — | 7.0 | 7.0 | 7.0 |
| (4) Talc treated with a fluorine compound* | — | 5.0 | 5.0 | — | 5.0 | 5.0 | 5.0 |
| (5) Color pigment | q.s. | q.s. | q.s. | q.s. | q.s. | q.s. | q.s. |
| (6) Soybean phospholipid | 1.0 | 1.0 | 1.0 | — | 1.0 | 1.0 | 1.0 |
| (7) Polyoxyethylene sorbitan oleate | 1.0 | 1.0 | 1.0 | — | 1.0 | 1.0 | 1.0 |
| (8) Trioctanoic glyceride | 2.0 | 2.0 | 2.0 | — | 2.0 | 2.0 | 2.0 |
| (9) Sucrose fatty acid ester | 1.0 | 1.0 | 1.0 | — | 1.0 | 1.0 | 1.0 |
| (10) Perfume | q.s. | q.s. | q.s. | q.s. | q.s. | q.s. | q.s. |
| (11) Preservative | q.s. | q.s. | q.s. | q.s. | q.s. | q.s. | q.s. |
| (12) 1,3-Butylene glycol | 10.0 | 10.0 | 10.0 | 10.0 | 10.0 | 10.0 | 10.0 |
| (13) Agar | 1.0 | 0.3 | 5.0 | 2.0 | — | — | 11.0 |
| (14) Carageenan | — | 0.1 | — | — | — | — | — |
| (15) Methylcellulose | — | — | — | — | 0.5 | — | — |
| (16) Carboxyvinyl polymer | — | — | — | — | — | 0.5 | — |
| (17) Glycyrrhizinic acid | — | — | — | — | 4.0 | — | — |
| (18) Sodium hydroxide | — | — | — | — | — | 0.1 | — |
| (19) Purified water | Balance | Balance | Balance | Balance | Balance | Balance | Balance |

*The method of treating with a fluorine compound

A slurry was produced from 50 g of a powder and 1,000 ml of water. Separately, an emulsion was prepared by adding 350 ml of water to 9 g of diethanolamine fluoroalkylphosphate (Asahi Guard AG530: trademark, manufactured by Asahi Glass Co.) and stirring the mixture.

This emulsion was slowly added to the slurry. The mixture was stirred and allowed to stand still at room temperature to complete the fluorine treatment.

Comparative Example 5

<Solid w/o-type foundation>

A w/o-type foundation was prepared from the following components.

| (Component) | % by weight |
|---|---|
| (1) Titanium dioxide | 15.0 |
| (2) Talc | 5.0 |
| (3) Silicic acid anhydride | 5.0 |
| (4) Color pigment | q.s. |
| (5) Ceresine | 3.0 |
| (6) Microcrystalline wax | 5.0 |
| (7) Squalane | 10.0 |
| (8) Trioctanoic glyceride | Balance |
| (9) Methylpolycyclosiloxane | 20.0 |
| (10) Sorbitan monooleate | 1.0 |
| (11) Polyoxyethylene sorbitan oleate | 1.0 |
| (12) Soybean phospholipid | 0.5 |
| (13) Preservative | q.s. |
| (14) 1,3-Butylene glycol | 5.0 |
| (15) Purified water | 15.0 |
| (16) Perfume | q.s. |

(Method of preparation)

A. Components (5) to (12) were heated and dissolved, and components (1) to (4) were added to the solution. The mixture was blended to disperse.

B. Components (13) to (15) were heated and dissolved.
C. Solution B was added to solution A to emulsify. After the addition of component (16), the emulsion was filled in a container and cooled. The same molding method as used for molding the cosmetic compositions of Examples 1–3 was adopted.

Test Example 1

Hardness, shape-retention ability and feel during use were evaluated on the foundations prepared in Examples 1–3 and Comparative Examples 1–5. The results are shown in Table 2.

(Method of Evaluation)

(1) Hardness

The stress ($g/cm^2$) was measured when a cylindrical adapter (cross-section diameter 10 mm$\phi$) was immersed for a specified distance (2 mm) at a specified speed (6 cm/sec) using a rheometer manufactured by Fudo Industries, Ltd. The value of the stress was taken as the hardness.

Normally, it is desirable that solid cosmetic compositions have a hardness in the range of 20 to 2,000 g/cm², when measured by the above method. If the hardness is smaller than 20 g/cm² the shape-retention capability as a solid cosmetic is poor; if it is greater than 2,000 g/cm² it is difficult for the cosmetic composition to attach to fingers or applicators when used.

(2) Shape-retention capability

Compositions were filled into a cylindrical dish-type container with a diameter of 50 mm and a depth of 10 mm and stored at 50° C. for 24 hours. The compositions which remained solid were rated as good (AAA) and those which lost solidity were rated as bad (CCC).

(3) Feel during use

A test for evaluating usability was carried out by 10 expert panelists. Each composition was evaluated in terms of releasability, wateriness, and the like, and rated by each panelist according to the following criteria. The mean value of ten panelists was adopted in the judgment.

Evaluation criteria:

Very good: 3

Good: 2

Fair: 1

Bad: 0

Judgment:

AAA: 2 or more

BBB: 1 or more but less than 2

CCC: less than 1

(Results)

| (Component) | % by weight |
|---|---|
| (12) Gelatin | 1.5 |
| (13) Purified water | Balance |

*The method of the silicone treatment

A powder and methylhydrogenpolysiloxane (2 parts for 98 parts of the powder) was added to isopropyl alcohol and treated with heating at 120° C. for 2 hours.

(Method of preparation)

A. Components (9) to (13) were heated and dissolved.

B. Components (1) to (7) were heated and blended, added to solution A, and blended to disperse.

Component (8) was added to dispersion B, and the mixture was filled in a container and cooled. The same molding method as used for molding the cosmetic compositions of Examples 1–3 was adopted.

Example 5

<Preparation of rouge>

| (Component) | % by weight |
|---|---|
| (1) Titanium dioxide | 5.0 |
| (2) Titanated mica | 5.0 |
| (3) Sericite | 5.0 |
| (4) Talc | 10.0 |
| (5) Color pigment | q.s. |
| (6) Polyoxyethylene castor oil (3EO) | 1.0 |
| (7) Soybean phospholipid | 1.0 |

TABLE 2

| Items | Examples | | | Comparative Examples | | | | |
|---|---|---|---|---|---|---|---|---|
| | 1 | 2 | 3 | 1 | 2 | 3 | 4 | 5 |
| Hardness (g/cm²) | 150 | 60 | 1600 | 480 | 0 | 0 | 2200 | 180 |
| Shape retention | AAA | AAA | AAA | AAA | CCC | CCC | AAA | AAA |
| Releasability | AAA | AAA | AAA | AAA | CCC | CCC | CCC | AAA |
| Wateriness | AAA | AAA | AAA | AAA | AAA | AAA | BBB | CCC |
| Freshness | AAA | AAA | AAA | AAA | AAA | AAA | BBB | CCC |
| Fitness | AAA | AAA | AAA | CCC | BBB | AAA | AAA | BBB |
| Natural finish | AAA | AAA | AAA | CCC | AAA | AAA | BBB | CCC |
| Water resistivity | AAA | AAA | AAA | CCC | AAA | AAA | BBB | AAA |

As can be seen from Table 2, the o/w-type foundations of the present invention impart an excellent feel during use, while maintaining their properties as a solid cosmetic composition. In addition, they exhibit superior usability, if the surface thereof is treated by the method of the present invention.

Example 4

<Preparation of eyeshadow>

| (Component) | % by weight |
|---|---|
| (1) Silicone-treated titanium dioxide* | 2.0 |
| (2) Silicone-treated titanated mica* | 10.0 |
| (3) Silicone-treated sericite* | 3.0 |
| (4) Color pigment | 2.0 |
| (5) Sorbitan sesquioleate | 2.0 |
| (6) Squalane | 1.0 |
| (7) Candellila wax | 1.0 |
| (8) Perfume | q.s. |
| (9) Preservative | q.s. |
| (10) 1,3-Butylene glycol | 5.0 |
| (11) Agar | 0.5 |

-continued

| (Component) | % by weight |
|---|---|
| (8) Starch fatty acid ester | 0.5 |
| (9) Isocetyl stearate | 5.5 |
| (10) Perfume | q.s. |
| (11) Preservative | q.s. |
| (12) 1,3-Butylene glycol | 5.0 |
| (13) Gelatin | 3.0 |
| (14) Purified water | Balance |

(Method of preparation)

A. Components (11) to (14) were heated and dissolved.

B. Components (1) to (9) were heated and blended, added to solution A, and blended to disperse.

C. Component (10) was added to dispersion B, and the mixture was filled in a container and cooled. The same molding method as used for molding the cosmetic compositions of Examples 1–3 was adopted.

Example 6

<Preparation of sweat suppressing cream>

| (Component) | % by weight |
|---|---|
| (1) Trioctanoic glyceride | 2.0 |
| (2) Squalane | 1.0 |
| (3) Microcrystalline wax | 1.0 |
| (4) Sucrose fatty acid ester | 1.0 |
| (5) Polyoxyethylene sorbitan oleate | 1.0 |
| (6) Color pigment | q.s. |
| (7) Perfume | q.s. |
| (8) Preservative | q.s. |
| (9) 1,3-Butylene glycol | 10.0 |
| (10) Agar | 1.5 |
| (11) 1-Menthol | 0.1 |
| (12) Purified water | Balance |

(Method of preparation)

A. Components (1) to (7) were heated and blended.

B. Components (8) to (12) were heated and dissolved.

C. Solution A was added to solution B, and the mixture was blended, filled in a container, and cooled. The same molding method as used for molding the cosmetic compositions of Examples 1–3 was adopted.

Example 7

<Preparation of sun screening cream>

| (Component) | % by weight |
|---|---|
| (1) Silicone-treated micronized titanium dioxide | 5.0 |
| (2) Soybean phospholipid | 1.0 |
| (3) Polyoxyethylene sorbitan oleate | 1.0 |
| (4) Trioctanoic glyceride | 2.0 |
| (5) Sucrose fatty acid ester | 1.0 |
| (6) Perfume | q.s. |
| (7) UV absorbent | 3.0 |
| (8) Preservative | q.s. |
| (9) 1,3-Butylene glycol | 10.0 |
| (10) Gelatin | 3.0 |
| (11) Xanthane gum | 0.1 |
| (12) Purified water | Balance |

(Method of preparation)

A. Components (8) to (12) were heated and dissolved.

B. Components (1) to (7) were heated and dissolved.

C. Solution B was added to solution A, and the mixture was blended, filled in a container, and cooled. The same molding method as used for molding the cosmetic compositions of Examples 1–3 was adopted.

Example 8

<Foundation>

| (Component) | % by weight |
|---|---|
| (1) Titanium dioxide treated with a fluorine compound* | 7.0 |
| (2) Talc treated with a fluorine compound* | 5.0 |
| (3) Sericite treated with a fluorine compound* | 3.0 |
| (4) Color pigment | q.s. |
| (5) Soybean phospholipid | 0.5 |
| (6) Sorbitan sesquioleate | 2.0 |
| (7) Trioctanoic glyceride | 2.0 |
| (8) Microcrystalline wax | 1.0 |
| (9) Perfume | q.s. |
| (10) Preservative | q.s. |
| (11) 1,3-Butylene glycol | 10.0 |
| (12) Agar | 1.0 |
| (13) Carboxyvinyl polymer** | 0.2 |
| (14) Triethanolamine | 0.2 |
| (15) Purified water | Balance |

*The method of treating with a fluorine compound

A slurry was produced from 50 g of a powder and 1,000 ml of water. Separately, an emulsion was prepared by adding 350 ml of water to 9 g of diethanolamine fluoroalkylphosphate (Asahi Guard AG530: trademark, manufactured by Asahi Glass Co.) and stirring the mixture. This emulsion was slowly added to the slurry and blended.

**Carbopole 940 (trademark, manufactured by Goodrich Chemical Co.)

(Method of preparation)

A. Components (10) to (15) were heated and dissolved.

B. Components (1) to (8) were heated and blended, and the blend was added to solution A to disperse.

C. Component (9) was added to Solution B, and the mixture was blended, filled in a container, and cooled.

Example 9

<Preparation of eyeshadow>

| (Component) | % by weight |
|---|---|
| (1) Silicone-treated titanium dioxide* | 2.0 |
| (2) Silicone-treated titanated mica* | 10.0 |
| (3) Silicone-treated sericite* | 3.0 |
| (4) Color pigment | 2.0 |
| (5) Sorbitan sesquioleate | 2.0 |
| (6) Squalane | 1.0 |
| (7) Candellila wax | 1.0 |
| (8) Perfume | q.s. |
| (9) Preservative | q.s. |
| (10) 1,3-Butylene glycol | 5.0 |
| (11) Agar | 0.5 |
| (12) Gelatin | 1.5 |
| (13) Sodium polyvinylpyrrolidone methacrylate | 0.1 |
| (14) Purified water | Balance |

*The silicone treatment was carried out in the same manner as in Example 4.

(Method of preparation)

A. Components (9) to (14) were heated and dissolved.

B. Components (1) to (7) were heated and blended, added to solution A, and blended to disperse.

C. Component (8) was added to dispersion B, and the mixture was blended, filled in a container, and cooled. The same molding method as used for molding the cosmetic compositions of Examples 1–3 was adopted.

Example 10

<Preparation of base cream>

| (Component) | % by weight |
|---|---|
| (1) Polyoxyethylene castor oil (3EO) | 1.5 |
| (2) Dimethylpolysiloxane | 0.5 |
| (3) Perfume | q.s. |
| (4) Preservative | q.s. |
| (5) Gelatin | 2.5 |
| (6) Carboxyvinyl polymer* | 0.8 |
| (7) Sodium hydroxide | 0.2 |
| (8) Glycerine | 3.0 |
| (9) Purified water | Balance |

*Carbopole 940 (trademark, manufactured by Goodrich Chemical Co.)

(Method of preparation)

A. Components (4) to (9) were heated and dissolved.

B. Components (1) and (2) were added to solution A and blended to disperse.

C. Component (3) was added to dispersion B, and the mixture was blended, filled in a container, and cooled.

Test Example 2

Surface processing test:

Suitability of various materials as a sheet material was evaluated using a cosmetic having the same composition as the foundation prepared in Example 1 according to the following method.

(Method)

The cosmetic composition was heated to melt, filled into a container and, after the attachment of the sheet material, cooled to solidify, whereupon the sheet material was peeled off. Ease of release after solidification, the conditions of the surface after peeling, and attachability of the foundation to a sponge were evaluated.

(Evaluation)

Moldability (ease of peeling):

AAA: Good (The amount adhering to the sheet material was small)

BBB: Bad (The amount adhering to the sheet material was large)

Surface conditions:

AAA: Uniform

BBB: Non-uniform (there were irregularities in peeling)

Usability (attachability to a sponge)

AAA: Attaches to the sponge

BBB: Does not attach to the sponge (Results)

Test Example 3

Test of tightness test between the container and cosmetic composition

Tightness between the container and the cosmetic composition was investigated using the containers of the present invention in which various water-absorbing materials are secured to the receptacle portion and conventional containers with no water-absorbing material secured thereto. The solid o/w-type cosmetic composition prepared in Example 8 was filled into these containers. The test consisted of a usability test under presumed normal conditions of use and a drop-impact test wherein conditions under which the containers were dropped were inferred. In the usability test, the cosmetic composition was repeatedly manipulated with a sponge in an attempt to take up it from the container. The cases where the cosmetic composition did not rotate in the container or was not released therefrom were rated as acceptable (AAA), and the cases where the cosmetic composition rotated or was released were rated as failed (BBB). In the drop-impact test, a dish-like container as shown in FIG. 6, held in a compact, was dropped straight down from a 1 m height. The cases where the cosmetic composition was not released or dislocated were rated as acceptable (AAA), and the cases where the composition was released or dislocated were rated as failed (BBB). The results are shown in Table 4.

TABLE 3

| Material | Water-carrying rate (%) | Moldability | Surface conditions | Usability |
| --- | --- | --- | --- | --- |
| (1) Acetate textile | 79 | AAA | AAA | AAA |
| (2) Nylon textile (100 mesh) | 52 | AAA | AAA | AAA |
| (3) Polyester textile | 83 | AAA | AAA | AAA |
| (4) Acryl textile | 65 | AAA | AAA | AAA |
| (5) Cotton textile | 318 | BBB | BBB | AAA |
| (6) Japanese paper | 947 | BBB | BBB | AAA |
| (7) Rayon non-woven sheet | 892 | BBB | BBB | AAA |
| (8) Linen textile | 290 | BBB | BBB | AAA |
| (9) No surface treatment | — | — | AAA | BBB |

The above results confirmed that materials having too high an affinity to the cosmetic composition adhered to it and could not be completely peeled off after solidification by cooling, and the products had no commercial value.

TABLE 4

| | Receptacle portion | | Water-absorbing material | Usability test | Drop-impact test |
| --- | --- | --- | --- | --- | --- |
| | Material | Rib | | | |
| Invention container | | | | | |
| 1 | PET | Present | Rayon non-woven textile | AAA | AAA |
| 2 | PET | Absent | Rayon non-woven textile | AAA | AAA |
| 3 | PET | Present | Cotton non-woven textile | AAA | AAA |
| 4 | PET | Present | Japanese paper | AAA | AAA |
| 5 | PET | Absent | Japanese paper | AAA | AAA |
| 6 | PET | Present | Japanese paper-water-absorbing polymer complex | AAA | AAA |
| 7 | PET | Present | Kaolin | AAA | AAA |
| 8 | Al | Absent | Kaolin | AAA | AAA |

TABLE 4-continued

|  | Receptacle portion | | Water-absorbing material | Usability test | Drop-impact test |
| --- | --- | --- | --- | --- | --- |
|  | Material | Rib | | | |
| 9 | Al | Present | Calcium carbonate | AAA | AAA |
| 10 | Al | Absent | Gypsum | AAA | AAA |
| Comparative container | | | | | |
| 1 | PET | Present | Plastic non-woven textile | BBB | BBB |
| 2 | PET | Present | Nylon powder | BBB | BBB |
| 3 | PET | Present | Silicone powder | BBB | BBB |
| 4 | PET | Present | PMMA | BBB | BBB |
| 5 | PET | Present | Untreated | BBB | BBB |
| 6 | Al | Present* | Untreated | BBB | BBB |
| 7 | Al | Present | Untreated | BBB | BBB |
| 8 | AS | Present | Untreated | BBB | BBB |
| 9 | PP | Present | Untreated | BBB | BBB |

PET: Polyethylene terephthalate, Al: aluminum, AS: Acrylonitrile-styrene resin, PP: Polypropylene, PMMA: Polymethylmethacrylate
*A rib is provided only on the side wall.

As can be seen from the above results, the cosmetic container of the present invention in which a water-absorbing material is secured in the receptacle was found to be able to hold cosmetic compositions more tightly and to have better usability.

As illustrated above, the o/w-type solid cosmetic composition of the present invention imparts a fresh feel during use, and exhibits excellent affinity to the skin, a good make-up finish and a superb moisturizing effect, while excelling in usability and portability.

Because the molding method of the present invention can produce a non-continuous cosmetic surface with the inner texture exposed thereon, it is easy to take up the cosmetic composition with an applicator. This further improves the usability of the o/w-type solid cosmetic composition of the present invention.

In addition, the container of the present invention can stably hold aqueous-type solid cosmetic compositions containing water such as the o/w-type solid cosmetic composition of the present invention.

Obviously, numerous modifications and variations of the present invention are possible in light of the above teachings. It is therefore to be understood that within the scope of the appended claims, the invention may be practiced other than as specifically described herein.

What is claimed is:

1. A solid cosmetic composition consisting essentially of an oil-in-water composition of,
    (a) a water-soluble solidifying agent consisting of agar,
    (b) an oil component,
    (c) water, and
    (d) a cosmetic powder.

2. The solid cosmetic composition of claim 2, wherein the cosmetic powder is selected from the group consisting of titanium dioxide, talc, mica, kaolin, magnesium carbonate, calcium carbonate, aluminum silicate, magnesium silicate, calcium silicate, zinc oxide, red iron oxide, yellow iron oxide, black iron oxide, ultramarine blue, prussian blue, tar pigment, natural pigments, titanated mica, iron oxide titanated mica, bismuth oxychloride, nylon powder and silk powder.

3. A solid cosmetic composition consisting essentially of an oil-in-water composition of,
    (a) a water-soluble solidifying agent consisting of agar,
    (b) an oil component,
    (c) water,
    (d) a cosmetic powder, and
    (e) a water-soluble adhesive.

4. The solid cosmetic composition of claim 3, wherein the cosmetic powder is selected from the group consisting of titanium dioxide, talc, mica, kaolin, magnesium carbonate, calcium carbonate, aluminum silicate, magnesium silicate, calcium silicate, zinc oxide, red iron oxide, yellow iron oxide, black iron oxide, ultramarine blue, prussian blue, tar pigment, natural pigments, titanated mica, iron oxide titanated mica, bismuth oxychloride, nylon powder and silk powder.

* * * * *